US009549984B2

(12) United States Patent
Weinrich et al.

(10) Patent No.: US 9,549,984 B2
(45) Date of Patent: Jan. 24, 2017

(54) PROBIOTIC ORAL DOSAGE FORMS AND METHOD OF ENHANCING THE STABILITY, THEREOF

(71) Applicant: Little Calumet Holdings, LLC, Silver Spring, MD (US)

(72) Inventors: Karl P. Weinrich, Parkland, FL (US); E. Frank Hodal, Jr., Silver Spring, MD (US)

(73) Assignee: Little Calumet Holdings, LLC, Beltsville, MD (US)

( * ) Notice: Subject to any disclaimer, the term of this patent is extended or adjusted under 35 U.S.C. 154(b) by 0 days.

(21) Appl. No.: 14/803,647

(22) Filed: Jul. 20, 2015

(65) Prior Publication Data

US 2015/0359894 A1 Dec. 17, 2015

Related U.S. Application Data (62) Division of application No. 11/528,893, filed on Sep. 27, 2006, now Pat. No. 9,084,434.

(51) Int. Cl.
| | | |
|---|---|---|
| A61K 47/26 | (2006.01) |
| A61K 9/20 | (2006.01) |
| A61K 35/745 | (2015.01) |
| A61K 35/747 | (2015.01) |
| A23L 29/30 | (2016.01) |
| A23L 33/105 | (2016.01) |
| A23L 33/135 | (2016.01) |

(52) U.S. Cl.
CPC ............... *A61K 47/26* (2013.01); *A23L 29/37* (2016.08); *A23L 33/105* (2016.08); *A23L 33/135* (2016.08); *A61K 9/2018* (2013.01); *A61K 35/745* (2013.01); *A61K 35/747* (2013.01); *A23V 2002/00* (2013.01)

(58) Field of Classification Search
CPC .................. A23V 2002/00; A23V 2200/3202; A23V 2200/3204; A23V 2200/32; A23V 2250/28; A23V 2250/21166; A23V 2250/64; A61K 31/702; A61K 2300/00; A61K 31/715; A61K 31/7016; A61K 35/745; A61K 35/747; A61K 9/4825; A61K 31/736; A61K 33/08; A61K 35/742; A61K 36/185; A61K 36/20; A61K 36/28; A61K 36/31; A61K 36/48; A61K 36/483; A61K 36/63; A61K 36/68; A61K 36/88
See application file for complete search history.

(56) References Cited

U.S. PATENT DOCUMENTS

| | | |
|---|---|---|
| 3,436,407 A | 4/1969 | Masquelier et al. |
| 4,518,696 A | 5/1985 | Gehrman et al. |
| 4,698,360 A | 10/1987 | Masquelier |
| 5,466,463 A | 11/1995 | Ford |
| 5,614,209 A | 3/1997 | Ford |
| 5,633,012 A | 5/1997 | Ford |
| 5,635,202 A | 6/1997 | Ford |
| 5,733,568 A | 3/1998 | Ford |
| 6,254,886 B1 | 7/2001 | Fusca et al. |
| 6,706,287 B2 | 3/2004 | Ranganathan et al. |
| 7,214,396 B2 | 5/2007 | Rivier |
| 2003/0118642 A1 | 6/2003 | Norman et al. |
| 2003/0215502 A1 | 11/2003 | Pruss et al. |
| 2004/0013767 A1 | 1/2004 | Norman et al. |
| 2004/0197277 A1 | 10/2004 | Gonzales |
| 2004/0223956 A1 | 11/2004 | Naidu et al. |
| 2006/0093592 A1 | 5/2006 | Cheruvanky et al. |
| 2006/0182727 A1 | 8/2006 | Yamahira et al. |
| 2007/0269515 A1 | 11/2007 | Henriksen et al. |
| 2008/0267933 A1 | 10/2008 | Ohlson et al. |
| 2009/0162322 A1 | 6/2009 | Rudolph et al. |

FOREIGN PATENT DOCUMENTS

| | | |
|---|---|---|
| JP | 60023321 A | 2/1985 |
| JP | 62-207286 | 9/1987 |
| JP | 63227507 A | 9/1988 |
| JP | 5255097 A | 10/1993 |
| JP | 11209296 A | 8/1999 |
| JP | 2001089397 A | 4/2001 |
| JP | 2001169749 A | 6/2001 |
| JP | 2002095409 | 4/2002 |
| WO | WO-9830235 A1 | 7/1998 |
| WO | WO-01/95918 | 12/2001 |
| WO | WO-02/05829 | 1/2002 |

(Continued)

OTHER PUBLICATIONS

Mallinckrodt Baker, Inc. "Mannitol Material Data Sheet", *MSDS* No. M0806 Aug. 20, 2008.

Liesbeth Masco et al., "Polyphasic taxonomic analysis of Bifidobacterium animalis and Bifidobacterium lactis reveals relatedness at the subspecies level: reclassification of Bifidobacterium animalis as *Bifidobacterium animalis* subsp. *animalis* subsp. nov. and Bifidobacterium lactis as *Bifidobacterium animalis* subsp. *lactis* subsp. Nov.", *International Journal of Systematic and Evolutionary Microbiology*, (2004), vol. 54, pp. 1137-1143.

Marcel B. Roberfroid "Prebiotics and probiotics: are they functional foods?", *Am J Clin Nutr*, (2000), vol. 71(suppl), pp. 1682S-1687S.

(Continued)

*Primary Examiner* — Debbie K Ware (74) *Attorney, Agent, or Firm* — Cooley LLP; Matthew Pavao (57) ABSTRACT

Provided are probiotic compositions that have enhanced stability under various storage conditions. The stability of the probiotic compositions is enhanced through the addition of various agents and excipients. Examples of agents and excipients that may be used to enhance the stability of probiotic compositions include prebiotics, such as the sugar alcohols mannitol, sorbitol, and lactitol, and/or phytonutrients such as oligomeric proanthocyanidins (OPCs). The probiotic compositions may be formulated into oral dosage forms such as tablets, caplets, and capsules, or manufactured as a chewing gum or as a powder formulation that may be dissolved in a liquid such as water, milk, juice, or yogurt.

17 Claims, 1 Drawing Sheet

(56) References Cited

FOREIGN PATENT DOCUMENTS

| WO | WO-2005/032591 | 4/2005 |
| WO | WO-2005/060937 | 7/2005 |

OTHER PUBLICATIONS

Roberfroid M. et al., "The Biochemistry of Oligofructose, a Nondigestible Fiber: An Approach to Calculate Its Caloric Value", *Nutrition Reviews*, vol. 51, No. 5, (May 1993), pp. 137-146.
http://pronutrition.org/archive/200406/msg00002.php.

PROBIOTIC ORAL DOSAGE FORMS AND METHOD OF ENHANCING THE STABILITY, THEREOF

CROSS-REFERENCE TO RELATED APPLICATION

This application is a Divisional of U.S. patent application Ser. No. 11/528,893, now U.S. Pat. No. 9,084,434, filed on Sep. 27, 2006, the contents of which is incorporated herein by reference in its entirety.

TECHNICAL FIELD

This invention relates generally to probiotic formulations and more specifically to probiotic oral dosage forms that remain stable under storage conditions.

BACKGROUND OF THE INVENTION

The gastrointestinal ("GI") tract is a complex microecosystem in which the mucosal lining of the host coexists with billions of microorganisms that live on or are attached to the lining. Among the microorganisms that inhabit the GI tract are "probiotic" bacteria, which help to maintain the health of the GI tract of the host organism. Within the GI tract of the host, probiotic bacteria are provided with shelter and support, and copious amounts of food substrates and in return, they offer the host a variety of potential therapeutic uses including replacing intestinal bacteria destroyed by antibiotics; aiding digestion and suppressing disease-causing bacteria; preventing and treating diarrhea, including infectious diarrhea, particularly from rotavirus (a virus that commonly causes diarrhea in children); treating overgrowth of "bad" organisms in the gastrointestinal tract (a condition that tends to cause diarrhea and may occur from use of antibiotics); alleviating symptoms of irritable bowel syndrome and, possibly, inflammatory bowel disease (such as Crohn's disease and ulcerative colitis); preventing and/or reducing the recurrence of vaginal yeast infections, urinary tract infections, and cystitis (bladder inflammation); improving lactose absorption digestion in people who are lactose intolerant; and enhancing the immune response. Because probiotics have many beneficial uses, there is a need in the art for probiotic supplements.

Among the probiotics that may be included in a supplement, are *Lactobacillus acidophilus, L. bulgaricus, L. casei, L. fermentum, L. paracasei, L. plantarum, L. rhamnosus, L. salivarius, Bifidobacterium bifidum, B. infantis, B. animalis* subsp. *lactis, B. longum, Streptococcus thermophilis, Enterococcus faecalis,* and *E. faecium,* all of which are found in the GI and vaginal tracts of humans. The *lactobacillus* species are gram-positive lactic acid bacteria that absorb lactose and other monosaccharides in the intestinal tract to produce lactic acid, which has the beneficial effect of lowering the pH of the organs making the environment of the organs hostile for the growth of harmful bacterial. The *bifidobacterium* species are the first species of microorganisms to colonize the sterile colon of a newborn baby that is nursed by its mother. Bifidobacteria use the mechanism of crowding to digest the nutrients that otherwise harmful bacteria would use for reproduction. Probiotic supplements may have up to approximately 10 billion colony forming units per supplement.

*L. acidophilus* in particular has the additional beneficial effect of producing the anti-microbial substances (i.e., natural antibiotics) acidolin, acidolphilin, lactocidin, and bacteriocin, which increase the immune system's resistance against fungus, such as *Candida albican,* and the harmful bacterial species *Escherichia coli, Staphylococcus aureus,* and *salmonella.*

*L. bulgaricus* enhances the digestibility of proteins and milk products, aids in the production of natural antibiotics, and has been used to treat gastrointestinal disorders such as enterocolitis.

*L. casei* has been found to have protective activity against pathogenic *listeria* bacteria.

*L. fermentum* has been found to prevent human immunodeficiency virus ("HIV") from infecting immune cells in infants (From Reuters Health, May 25, 2004, author Karla Gale, available at http://pronutrition.org/archive/200406/msg00002.php).

*L. plantarum* helps produce lactolin, a natural antibiotic, and synthesizes L-lysine.

*L. salivarius* is a facultative bacterium (i.e., a bacterial species that survives and grows in both anaerobic and aerobic environments) that is most abundant in the mouth and gums. *L. salivarius* has several advantages as a probiotic: it has the ability to break down undigested protein and disengage the toxins produced by protein putrefactions; it is useful to prevent and fight *Helicobacter pylori,* which is known to be a cause of ulcers); and because its population doubles every 20 minutes, smaller amounts of the probiotic may be administered to a patient thus lending an economic advantage to the use of the probiotic.

*L. rhamnosus* has excellent stability over a wide range of temperatures and pH levels; it relieves hypersensitivity reactions and intestinal inflammation in individuals with eczema and food allergies.

*B. animalis* is a probiotic bacterium that plays a role in intestinal mucosal defense. *B. animalis* has two subspecies: *B. animalis* subsp. *animalis* and *B. animalis* subsp. *lactis,* both of which prior to 2004 were referred to as *B. animalis* and *B. animalis* subsp. *lactis.* Masco et al., INT'L J SYST EVOL BIOL 54:1137-1143 (2004). Because *B. animalis* subsp. *animalis* only grows in anaerobic environments and is incapable of growth in milk cultures, it is not useful as a probiotic. By contrast, *B. animalis* subsp. *lactis,* which is a lactic acid bacterium characterized by its high oxygen resistance and production of considerable amounts of formate, grows well in milk cultures and thus, is a useful probiotic. *B. animalis* subsp. *lactis* is added to infant formulas to ensure that newborn babies not being nursed have sufficient colonization of bifidobacteria and is the only *bifidobacterium* species that is found in yogurt cultures.

*B. bifidum* inhibits the growth of the harmful bacterial species *salmonella, listeria, shigella, E. coli,* and *Clostridium perfringens* by consuming their nutrients, such as for example, ferrous ions, which many harmful bacterial species require for growth. *B. bifidum* also synthesizes some vitamins and aids in the absorption of minerals such as calcium, magnesium, and zinc.

*B. infantis* is the first probiotic to colonize the sterile digestive tract of an infant that is nursed by its mother. For infants that are formula fed, this probiotic may be administered in supplemental form in order to ensure that the newborn has the proper intestinal flora.

*B. longum* biovar *longum* (referred to as *B. longum*) has been found to be able to eliminate nitrates from the intestinal tract.

*S. thermophilis* generates lactase activity, facilitating the digestion of lactose in milk.

*E. faecalis* and *E. faecium* are both lactic acid bacteria that have inhibitory effects against enteropathogens such as *E. coli*, salmonellae, shigellae and clostridia.

U.S. Pat. No. 4,518,696 to Gehrman et al. teaches the use of sunflower oil as a liquid suspending medium for preparing dry viable *lactobacillus* cells that are stable at room temperature.

U.S. Pat. No. 5,466,463 to Ford teaches a vaginal suppository containing an antimicrobial agent and a viable colony of microencapsulated lactobacilli bacteria; the bacteria are microencapsulated to protect them from the action of the antimicrobial agent.

U.S. Pat. Nos. 5,614,209; 5,633,012; 5,635,202; and 5,733,568 all to Ford teach microencapsulated lactobacilli bacteria for oral and topical administration to mammals that have $10^3$ viable microencapsulated lactobacilli in each unit dose.

U.S. Pat. No. 6,706,287 to Ranganathan et al. teaches microencapsulated and/or enteric-coated probiotics, such as *lactobacillus* and bifidium bacteria species, that are capable of metabolizing urea and ammonia to amino acids.

A disadvantage of many of the probiotic formulations on the market is the poor shelf life of the formulations; accordingly, there is a need in the art for improved shelf life of probiotic formulations having live colonies of probiotic bacteria, such as for example, *lactobacillus* and *bifidobacterium*.

SUMMARY OF THE INVENTION

The present invention overcomes the need in the art by providing a probiotic composition that includes one or more agents and/or excipients that maximize the stability of the probiotics under storage conditions.

In one embodiment of the invention, there is provided a composition comprising at least one probiotic species in a carrier comprised of least two sugar alcohols selected from the group consisting of erythritol, lactitol, maltitol, mannitol, sorbitol, and xylitol.

In another embodiment of the invention, there is provided a method of enhancing stability of a probiotic composition comprising combining at least one probiotic species with a carrier comprised of least two sugar alcohols selected from the group consisting of erythritol, lactitol, maltitol, mannitol, sorbitol, and xylitol.

In the composition and the method of the present invention, the carrier may further comprise a disintegrant, a glidant, and/or a lubricant. The disintegrant may be any suitable disintegrant such as for example, a disintegrant selected from the group consisting of sodium croscarmellose, crospovidone, gellan gum, hydroxypropyl cellulose, starch, and sodium starch glycolate. The glidant may be any suitable glidant such as for example, a glidant selected from the group consisting of silicon dioxide, colloidal silicon dioxide, and talc. The lubricant may be any suitable lubricant such as for example, a lubricant selected from the group consisting of calcium stearate, magnesium stearate, stearic acid, sodium stearyl fumerate, and vegetable based fatty acids. In the composition and method of the present invention, the carrier, is present in the composition in a range of approximately 30% w/w to approximately 98% w/w; this weight percentage is a cumulative weight percentage taking into consideration all ingredients present in the carrier.

In the composition and method of the present invention, the probiotic may be any probiotic species such as for example, a probiotic selected from the group consisting of *Lactobacillus acidophilus, L. bulgaricus, L. casei, L. para-casei, L. fermentum, L. plantarum, L. rhamnosus, L. salivarius, Bifidobacterium bifidum, B. infantis, B. animalis* subsp. *lactis, B. longum, Streptococcus thermophilis, Enterococcus faecalis*, and *E. faecium*. Combinations of probiotic species are also contemplated under the composition and method of the present invention such as for example, a combination of *L. acidophilus* and *B. animalis* subsp. *lactis*. The concentration of probiotics contemplated under the composition and method of the present invention is in a range of approximately $10^6$ to approximately $10^{10}$ colonies per dosage form; this concentration is an individual concentration range for each probiotic present in the composition.

In the composition and method of the present invention, the composition may further include a phytonutrient, such as for example, a phytonutrient is selected from catechins, polyphenols, and oligomeric proanthocyanidins (OPCs). Where the phytonutrient is OPC, it may be obtained from grape seed or pine bark and incorporated into the composition in a range of approximately 0.5% w/w to approximately 10% w/w.

In the composition and method of the present invention, the composition may further include a vitamin, a dietary mineral, and/or a trace mineral. The vitamin may be selected from the group consisting of vitamin A (retinol), vitamin $B_1$ (thiamine), vitamin $B_2$ (riboflavin), vitamin $B_3$ (niacin), vitamin $B_5$ (pantothenic acid), vitamin $B_6$ (pyridoxine), vitamin $B_7$ (biotin), vitamin $B_9$ (folic acid), vitamin $B_{12}$ (cyanocobalamin), vitamin C (ascorbic acid), vitamin $D_1$ (lamisterol), vitamin $D_2$ (ergocalciferol), vitamin $D_3$ (dihyrotachysterol), vitamin $D_4$ (7-dehydrositosterol), vitamin E (tocopherol), and vitamin K (naphthoquinone). The dietary mineral may be selected from the group consisting of calcium, chloride, magnesium, phosphorous, potassium, sodium, and sulfur. The trace mineral may be selected from the group consisting of chromium, cobalt, copper, fluorine, iodine, iron, manganese, molybdenum, selenium, and zinc.

The composition of the present invention may be an oral dosage form, a powder that is mixed into a liquid, or a chewing gum. Where the composition is an oral dosage form, the oral dosage form may be selected from the group consisting of tablets, caplets, and capsules, wherein the tablets and caplets may be solid or chewable. Where the composition is a powder, it may be mixed into a liquid that is selected from the group consisting of water, milk, juice, and yogurt. Where the composition is a chewing gum, the gum may be solf gum or hard chewing gum tablets.

By combining probiotic species with sugar alcohols, such as mannitol, sorbitol, alone or together with the additional sugar alcohol lactitol and/or a phytonutrient, such as OPC, the present inventors have discovered that the stability of probiotic formulations is surprisingly and unexpectedly increased under various storage conditions.

Additional aspects, advantages and features of the invention will be set forth, in part, in the description that follows, and, in part, will become apparent to those skilled in the art upon examination of the following, or may be learned by practice of the invention.

DETAILED DESCRIPTION OF THE INVENTION

Following is a description of exemplary embodiments of the present invention. The definitions set forth below are provided solely for the purpose of describing the exemplary embodiments and are not intended to limit the scope of the present invention. As the embodiments described herein are exemplary, it is to be understood that the invention as described contemplates modifications in the function, purpose, and/or structure of the exemplary embodiments.

As used in this specification and the appended claims, the singular forms "a," "an," and "the" include plural referents unless the context clearly dictates otherwise.

As used herein, the term "animal" refers to a non-human species and the term "organism" refers to both animal and human species. While the term "animal" as used herein will typically be used to refer mammals, the term is not exclusive to mammals and where appropriate may include both mammals and non-mammals.

The term "excipient" refers to an inert substance that is typically used as a diluent or vehicle for a drug or dietary supplement.

The term "probiotic" refers to bacterial genera that have a beneficial effect in animal organs, such as the human GI and vaginal tracts. The bacterial genera used most often as probiotics are lactobacilli and bifidobacteria; however, other beneficial bacterial species, such as *S. thermophilis* are also probiotics. After passage through the stomach and small intestine, some probiotics survive and become established transiently in the large bowel, where the colon's fermentation capacity is positively modified. See, e.g., Roberfroid, AM J CLIN NUTR 71(SUPPL):1682S-1687S (2000).

The probiotic species that may be used in the compositions of the present invention may be any known probiotic, such as, for example, *L. acidophilus, L. bulgaricus, L. casei, L. paracasei, L. fermentum, L. plantarum, L. rhamnosus, L. salivarius, B. bifidum, B. infantis, B. animalis* subsp. *lactis, B. longum, S. thermophilis, E. faecalis,* and *E. faecium.* It is to be understood that the foregoing list is intended only to be illustrative and not a limiting representation of the probiotics that may be included in the probiotic compositions of the present invention. In this respect, any additional probiotic species may also be used in the compositions of the present invention, such as, for example, any additional known and/or available *lactobacillus* or *bifidobacterium* species.

The term "prebiotic" refers a nondigestible food ingredient that beneficially affects the host by selectively stimulating growth and/or activity of one or more probiotic species in the colon, such as for example, lactobacilli and/or bifidobacteria. Because prebiotics have a chemical structure that resists digestion through the alimentary tract, they reach the colon as intact molecules where they are able to elicit systemic physiological functions and act as fermentable substrates for colonic microflora. Examples of prebiotics include fructooligosaccharides, such as inulin, which is extracted from chicory, artichokes, asparagus, dandelions, dahlias, endive, garlic, leeks, lettuce, and onions; transgalactosyloligosaccharides; glactosyllactose; isomaltooligosaccharides; raffinose; lactulose; lactitol (a sugar alcohol); and partially hydrolyzed guar gum. The most commonly used prebiotic is inulin. While inulin has been found to be a good substrate for *bacteroides* and *bifidobacterium* species (*B. bifidum* and *B. longum* excluded) it is not an excellent substrate for other probiotics. Roberfroid et al., NUTR. REV. 51:137-146 (1993). Where a prebiotic is combined with a probiotic, the resulting supplement is sometimes referred to as a "synbiotic."

An example of a prebiotic that may be used with the probiotic compositions of the present invention is the sugar alcohol lactitol, which is currently commercially used as a replacement sweetener for low calorie foods. Lactitol has two calories (9 kilojoules) per gram and approximately 40% of the sweetness of sugar. The United States Food and Drug Administration ("FDA") classifies lactitol, along with other sugar alcohols, which may or may not be prebiotics, i.e., erythritol, maltitol, mannitol, sorbitol, and xylitol, as "generally recognized as safe" ("GRAS").

As noted above, the choice of the prebiotic to be combined with a particular probiotic will be determined according to which prebiotic provides the most suitable substrate for a particular probiotic. When considering the use of a particular prebiotic, synergy between one or more prebiotics and/or synergy between one or more prebiotics and other ingredients should always be considered. Synergy between the prebiotics lactitol and OPC with the sugar alcohols mannitol and sorbitol is illustrated in the experiment set forth in Example 10.

In Example 10, the mannitol and sorbitol sugar alcohols described in the carbohydrate carrier system disclosed in U.S. Patent Publication No. 2003/0118642 A1 to Norman et al., which is incorporated by reference herein, were combined with *L. acidophilus* to form two probiotic batches (Table 27), which were tested for stability (Table 28). As a control, the PHARMABURST® product (SPI Polyols, New Castle, Del.), which is a commercially available product covered by the Norman et al. Patent Publication, was used as a carrier to prepare an *L. acidophilus* probiotic; PHARMABURST® includes the sugar alcohols mannitol and sorbitol. As shown in Table 28, mannitol and sorbitol alone were incapable of keeping *L. acidophilus* viable under the harsh storage conditions of 40° C./75% RH and as shown in Table 30, while PHARMABURST® was capable of keeping *L. acidophilus* viable for 2 weeks under the mild storage conditions of 25° C./60% RH, the viability was limited. By contrast, as shown in Tables 31 and 32 (Example 11), when lactitol and/or OPC were added to the *L. acidophilus* probiotic formulation of Table 29, *L. acidophilus* maintained a high level of stability for two weeks under the harsh storage conditions of 40° C./75% RH without a desiccant (see, Table 32, Batch E), indicating a synergistic effect between the sugar alcohols mannitol and sorbitol and the prebiotics lactitol and/or OPC. The foregoing indicates that *L. acidophilus* probiotics that are formulated to include at least the sugar alcohols mannitol and sorbitol in combination with lactitol and/or OPC results in probiotic compositions that have a long shelf-live.

Figure 1:
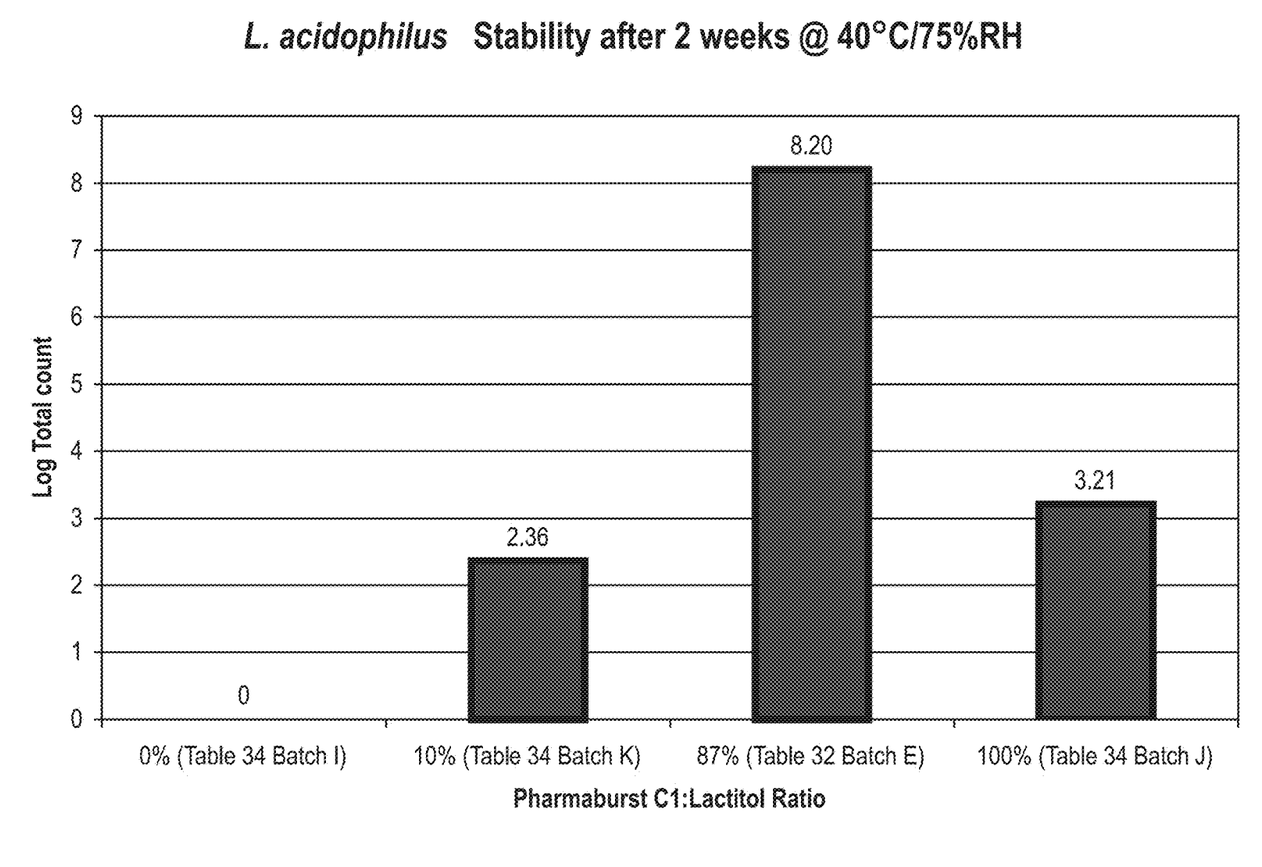
FIG. 1 is a bar graph showing the results of the *L. acidophilus* stability tests described in Examples 11 and 12 (Tables 32 and 34).

To determine if lactitol has a significant effect on the stability of *L. acidophilus*, three batches of *L. acidophilus* probiotic tablets were prepared as set forth in Table 33 (Example 12), one batch with *L. acidophilus* and lactitol (Batch I), a second with *L. acidophilus* and PHARMABURST® (Batch J), and a third with *L. acidophilus*, lactitol, and PHARMABURST® (Batch K). The results of Table 34 (Example 12) show that under the harsh conditions of 40° C./75% RH, lactitol alone was not effective in maintaining the stability of *L. acidophilus* whereas PHARMABURST® alone and the combination of a relatively low weight percent of PHARMABURST® in combination with lactitol showed some viable colonies of *L. acidophilus* after two weeks. A log graph comparing the stability test results of Batch E (Table 32) with Batches I, J, and K (Table 34) is shown in FIG. 1. As is shown in the graph, under the harsh storage conditions of 40° C./75% RH, after two weeks, 100% lactitol failed to stabilize *L. acidophilus*; 100% PHARMABURST® showed limited viability of *L. acidophilus*; a combination of 10% PHARMABURST® and 90% lactitol showed limited viability of *L. acidophilus*; and a combination of 87% PHARMABURST® and 13% lactitol showed significant viability of *L. acidophilus*. The results of the stability tests as shown in FIG. 1 indicate that at an optimal ratio, a synergistic effect occurs between the PHARMABURST® ingredients and lactitol.

The term "phytonutrient" refers to a nutrient derived from a plant source that has a beneficial effect on the health of the organism, i.e., the animal or human, taking the phytonutrient. Phytonutrients differ from nutrients in that they are not required for normal metabolism of the organism. Many phytonutrients are antioxidants that impart bright colors to fruits and vegetables. For example, lutein makes corn yellow, lycopene makes tomatoes red, carotene makes carrots orange, and anthocyanin makes blueberries blue. Both the bright colors and the antioxidant properties of phytonutrients are due to alternating single-bonded and double-bonded carbons. Phytonutrients that may be included in the probiotic formulations of the present invention include without limitation catechins, which are found in tea; polyphenols, which are found in fruit skins such as grape skin, apple skin, and orange skin; and oligomeric proanthocyanidins ("OPCs") which are found in fruits, vegetables, nuts, seeds, flowers, and bark, but which are generally extracted from grape seeds and/or pine bark. The isolation of OPC is described in U.S. Pat. Nos. 3,436,407 and 4,698,360, both to Masquelier et al. Tables 31 and 32 (Batch H) of Example 11 shows that the addition of OPC (without lactitol) to the *L. acidophilus* probiotic composition described therein maintained the stability of *L. acidophilus* at a very high level for two weeks under the harsh storage conditions of 40° C./75% RH without a desiccant. Within the context of the present invention, OPCs may be added to the probiotic compositions in a wide range, such as for example, from approximately 0.05% w/w to approximately 25% w/w; generally; however, a range of approximately 0.5% w/w to approximately 10% w/w should be sufficient for the OPC to show effect.

In addition to the foregoing, the present invention also includes the addition of at least one probiotic species in combination with at least one prebiotic and at least one OPC. As shown in Table 18 of Example 7, the addition of the prebiotic lactitol and the phytonutrient OPC to the *L. acidophilus* and *B. animalis* subsp. *lactis* probiotic composition described therein resulted in the highest stability count for the probiotic composition at 6 months under the storage conditions of 25° C./60% RH with a desiccant. Further, Batch I of Tables 31 and 32 of Example 11 demonstrate that the addition of the prebiotic lactitol and the phytonutrient OPC to the *L. acidophilus* probiotic composition described therein maintained the stability count of the *L. acidophilus* probiotic composition at a very high level for two weeks under the harsh storage conditions of 40° C./75% RH without a desiccant.

Additional ingredients that may be included with the probiotic combinations described above include vitamins, dietary minerals, trace minerals, and other phytonutrients. See Example 8, Tables 20-22.

Vitamins that may be included in the probiotic composition of the present invention include without limitation, vitamins such as vitamin A (retinol), vitamin $B_1$ (thiamine), vitamin $B_2$ (riboflavin), vitamin $B_3$ (niacin), vitamin $B_5$ (pantothenic acid), vitamin $B_6$ (pyridoxine), vitamin $B_7$ (biotin), vitamin $B_9$ (folic acid), vitamin $B_{12}$ (cyanocobalamin), vitamin C (ascorbic acid), vitamin $D_1$ (lamisterol), vitamin $D_2$ (ergocalciferol), vitamin $D_3$ (dihyrotachysterol), vitamin $D_4$ (7-dehydrositosterol), vitamin E (tocopherol), and vitamin K (naphthoquinone). The foregoing listing includes vitamin salts, such as for example, retinol acetate, retinol palmitate, and thiamine mononitrate.

Dietary minerals that may be included in the probiotic compositions of the present invention include without limitation, calcium, chloride, magnesium, phosphorous, potassium, sodium, and sulfur.

Trace minerals that may be included in the probiotic compositions of the present invention include without limitation, chromium, cobalt, copper, fluorine, iodine, iron, manganese, molybdenum, selenium, and zinc.

The probiotic compositions of the present invention may be manufactured into various formulations, such as for example, oral dosage forms, such as tablets, caplets, or capsules; chewing gum; or powders to be dissolved in a liquid.

As noted above, the probiotic compositions of the present invention may be formulated into oral dosage forms, such as tablets, caplets, or capsules. The probiotic tablets and caplets of the present invention may be formulated for swallowing or for chewing. In the latter case, the tablets and caplets should be prepared with flavoring. Where necessary, the flavored chewable tablets and caplets may include a sweetener, which may be an artificial or natural sweetener or both. The probiotic capsules of the present invention will be manufactured primarily for swallowing.

Procedures for preparing tablets, caplets, and capsules are known to those of ordinary skill in the art and include without limitation wet granulation, dry granulation, and direct compression (for tablets and caplets).

Wet and dry granulation is used to manufacture tablets, caplets, or capsules. With granulation techniques, a chilsonation is used to manufacture the powder for the dosage forms. A chilsonator houses grooved, rotating rollers that are pressed tightly against one another by hydraulic pressure. Raw materials are placed into the hopper of the chilsonator and are fed by a system of horizontal and vertical screws into the rollers. As materials pass through the grooves in the rollers, it is compacted under very high pressure and emerges from the chilsonator as dense sheets. The sheets are milled into a fine granular powder using a Fitz mill and then passed through a screen to produce a uniform free flowing granule. The chilsonation process results in a finished powder that is two to four times denser than the starting material, a feature that permits the ingredients to be fashioned into the desired dosage form.

With dry granulation, the powder may be incorporated into a gelatin capsule or it may be mixed with gelatin to form a tablet or caplet. With wet granulation, the powder is moistened thus creating large "chunks" of material that are subsequently dried and milled to convert the chunks to particles of a desired size for the manufacturing process. Once the particles of a desired size are obtained, the particles are incorporated into a gelatin capsule or mixed with gelatin to form a tablet or caplet.

Most direct compression formulations consist of three types of ingredients: an inert carrier that provides volume to the final dosage form; a lubricant that aids in the compression process; and the active ingredients. Carriers may be present in dosage forms in many ranges, from 0.5% w/w to 95% w/w. Within the context of the present invention, carriers used to formulate the probiotic compositions of the present invention will generally be in the range of approximately 30% w/w to approximately 98% w/w. The carrier used in the Examples is a PHARMABURST® carrier (SPI Polyols, New Castle, Del.).

With direct compression, the ingredients are mixed in a batch blender, such as a twin-shell or V-blender, and discharged into a bin (usually portable), which then feeds a chute to the tableting process. As an alternative to batch blending, in-bin blending is also used. With in-bin blending, the unmixed material is placed in a portable bin, which may contain internal baffles, and is tumbled; in-bin blending avoids the need to transfer the material from the blender to the portable container. In direct compression formulations, there is a wide particle-size distribution with the active agent usually being at the fine end of the range. To avoid segregation of the particles, reliable flow must be maintained in the bins at all time. To ensure that all tablets are of the highest quality, tablets must be sampled at regular intervals during production for active ingredient concentration, tablet hardness, and dissolution rates.

Direct compression may be used to make tablets and caplets for swallowing and also chewable tablets and caplets. With the latter, the hardness of the tablets and caplets will need to be reduced and the ingredients of the tablets and caplets will need to be adjusted to ensure that the tablets and caplets have a pleasant taste and pleasant mouth-feel. The taste of the chewable tablets and caplets may be adjusted through the use of various flavorings and sweeteners and the mouth-feel of the chewable tablets and caplets may be adjusted though the use of varying prebiotics, such as inulin, lactitol, mannitol, etc. The mouth feel of the chewable tablets must be adjusted to ensure that the when the tablet or caplet body is crushed, it folds into the flavored matrix; if the body is too brittle, it may fracture causing an uncomfortable sensation in the user's mouth. For chewable tablets, where taste is significant to user acceptability, the product should also have a pleasant odor when the bulk package is opened. Each of the features of the chewable tablet may be attained by adjusting the excipients until the desired properties are achieved.

Depending on the final size and characteristics of the tablets and caplets, i.e., size, hardness, brittleness, mouth feel for chewing, etc., two different direct compression machines may be used to manufacture the dosage forms. Single punch presses typically exhibit low compression speeds while rotary presses exhibit high compression speeds. The Examples describe the use of both a single punch press (Examples 1 and 2) and rotary presses (also called rotary machines; Examples 2-4 and 7-10).

The probiotic compositions of the present invention may also be incorporated into chewing gum. The chewing gum preferably includes a flavor and may be hard chewing gum or soft chewing gum. Where necessary, the flavored hard or soft chewing gum may include a sweetener, which may be an artificial or natural sweetener or both. Procedures for manufacturing gum are known to those of ordinary skill in the art.

Gum is traditionally made using four ingredients: a gum base, such as a resin obtained from pine trees; a natural sweetener, such as sugar, or an artificial sweetener; a softener, such as glycerin; and flavoring. The raw materials for the gum are mixed with a mixer while kept at a constant temperature during the prescribed processing time. Mixed gum materials are then sent to a hopper and extruded by twin screws to make a gum sheet. The inside and outside of the gum sheets are powdered to prevent sticking to the matching during rolling and packaging. During the extruding process, the gum sheet thickness is controlled with a roller. After extrusion, the gum sheet is scored and cut for proper sizing, passed through a cooling tunnel, and stacked on trays for packaging. Where the gum is a hard chewing gum, such as a chewing gum tablet, the gum is coated between the cutting and cooling steps. Specially designed machines are available for each of the steps; thus, gum can be made using a mixing machine, an extruding machine, a forming machine, a cooling machine, and a stacking machine.

Gum may also be prepared using the direct compression procedure described in U.S. Patent Publication No. 2004/0013767 to Norman and Amin, which is incorporated by reference herein. Under this procedure, a gum base, granulating agent, processing aid, and one or more lubricants are mixed and subjected to direct compression on a traditional tabletting machine. Sweeteners, colorings, and flavorings may also be added to the mixture. A commercially available mixture of polyol(s) and/or sugars in a gum base is sold commercially as PHARMAGUM® (SPI Polyols, Inc., New Castle, Del.). The direct compression procedure is particularly useful for preparing chewing gum tablets.

In both of the foregoing procedures, the probiotic is added during the initial mixing stage prior to extrusion or direct compression.

In addition to the foregoing, the probiotic compositions of the present invention may be prepared as a powder that is intended to be dissolved in a liquid, such as water, milk, juice, and yogurt. It is understood that the individual liquids may be mixed together where appropriate. For example, the probiotic formulation may be combined with fruit juice and yogurt or milk and yogurt to make probiotic yogurt shakes. The probiotic formulation may also be combined with milk and ice cream to make probiotic milk shakes. Flavorings for the probiotic liquid formulations contemplated under the invention are known to those of ordinary skill in the art.

Examples of excipients that may be used to formulate appropriate dosage forms include binders, disintegrants, lubricants, coatings, plasticizers, compression agents, wet granulation agents, and sweeteners, all of which are known to those of ordinary skill in the art to which the invention pertains. All of the following examples are provided by way of illustration and not limitation. Binders are used where appropriate to help the dosage form ingredients still together. Examples of binders include carbopol, povidone, and xanthan gum. Lubricants are generally always used in the manufacture of dosage forms by direct compression in order to prevent the compacted powder mass from sticking to the equipment during the tabletting or encapsulation process. Examples of lubricants include calcium stearate, magnesium stearate, stearic acid, sodium stearyl fumerate, and vegetable based fatty acids. Disintegrants aid in the break up of the compacted mass when placed in a fluid environment. Examples of disintegrants include sodium croscarmellose, crospovidone, gellan gum, hydroxypropyl cellulose, starch, and sodium starch glycolate. Coatings are used to control the solubility of the drug. Examples of coatings include carrageenan, cellulose acetate phthalate, ethylcelulose, gellan gum, matodextrin, methacrylates, methylcellulose, microcrystalline cellulose, and shellac. Plasticizers are used to control the release rate of the drug from the dosage form. Examples of plasticizers include citrate esters, dibutyl sebacate, diethyl phthalate, polyvinylacetate phthalate, and triacetin. Compression agents include calcium carbonate, dextrose, fructose, guar gum, honey, lactose, maltodextrin, maltose, mannitol, microcrystalline cellulose, molasses, sorbitol, starch, and sucrose. Wet granulation agents include calcium carbonate, lactose, maltodextrin, mannitol, microcrystalline cellulose, povidone, and starch. Sweeteners include aspartame, dextrose, fructose, honey, lactose, maltodextrin, maltose, mannitol, molasses, monoammonium glycyrrhizinate, sorbitol, sucralose, and sucrose. Excipients that are generally used in the manufacture of chewable tablets include by way of illustration and not limitation, dextrose, fructose, guar gum, lactose, maltodextrin, maltose, mannitol, microcrystalline cellulose, and sorbitol. As is evident from the foregoing list, many of the same ingredients may be used for various different purposes in various different dosage forms.

In each of the probiotic compositions described above, the probiotic should be present in a range of approximately $10^6$ colonies per dosage unit to approximately $10^{10}$ colonies per dosage unit, although higher counts are also acceptable. Where the probiotic composition is to be administered to an adult human being, i.e., a human being over the age of 16, the probiotic is preferably in the range of at least $10^9$, more preferably $10^{10}$ or even higher. Where the probiotic composition is to be administered to a child, i.e., a human being under the age of 16, the probiotic is preferably in the range of approximately $10^6$ to approximately $10^8$. The Examples set forth various studies to determine the conditions at which the probiotic compositions of the present invention have the longest duration. As is shown in Example 10, and as would be expected, the storage conditions play a significant difference in the duration of the probiotic compositions, c.f., the stability of the probiotic compositions at 25° C./60% RH, 30° C./65% RH, and 40° C./75% RH (Tables 16-18, 20-22 and 24-26). Further, the presence of a desiccant in the storage package may also make a difference under certain storage conditions, although, this is not always the case; cf., Tables 12, 13, 16-18. Examples of desiccants that can be used with the present invention include without limitation, silica gel (silicon dioxide), indicating silica gel (silica gel washed with cobalt chloride), montmorillonite clay, calcium oxide, calcium sulfate, activated alumina beads, and molecular sieve (e.g., aluminosilicate materials or synthetic compounds such as clays, porous glass, microporous charcoal, or active carbon).

The probiotic compositions of the present invention have widespread utility in the manufacture of various consumable commercial products that upon ingestion by a human or an animal will regulate their digestive systems by ensuring that the digestive tract is populated by live probiotic species. Because it is essential that probiotic species are viable upon ingestion, the enhanced stability of the probiotic species in the probiotic compositions of the present invention ensure that the probiotic compositions have the capability to reduce the number of pathogenic species in the colon. Examples of pathogenic bacteria that may be reduced through ingestion of the probiotic compositions of the present invention include without limitation, Campylobacter jejuni, E. coli, S. aureaus, Vibrio cholera, bacteroides, clostridia, klebsiella, listeria, proteus, salmonella, shigella, and veilloniella. An example of pathogenic yeast that may be reduced though ingestion of the probiotic compositions of the present invention include without limitation C. albicans. As previously noted, beneficial probiotic species, such as lactobacilli and bifidobacteria keep those potentially disease causing pathogens under control preventing disease-related dysfunctions.

All patent and non-patent publications mentioned herein, both supra and infra, are incorporated by reference in their entireties.

An advantage of the probiotic formulations of the presenting invention is that they are a pleasant-tasting product that may be consumed without water. Further, the probiotic formulations of the present invention are stable at room temperature and thus, do not need special conditions in order to improve or sustain the shelf life of the product.

EXPERIMENTAL

The following examples are put forth so as to provide those of ordinary skill in the art with a complete disclosure and description of how to make and use the compositions of the invention. The examples are intended as non-limiting examples of the invention.

The following examples will use, unless otherwise indicated, conventional techniques of pharmaceutical formulation, medicinal chemistry and the like, which are within the skill of the art. Such techniques are explained fully in the literature. Preparation of various types of pharmaceutical formulations are described, for example, in REMINGTON: THE SCIENCE AND PRACTICE OF PHARMACY, $20^{th}$ edition (Lippincott Williams & Wilkins, 2000) and Ansel et al., PHARMACEUTICAL DOSAGE FORMS AND DRUG DELIVERY SYSTEMS, $6^{th}$ Ed. (Media, Pa.: Williams & Wilkins, 1995).

In the examples that follow, efforts have been made to ensure accuracy with respect to numbers (e.g., amounts, temperature, etc.), but experimental error and deviations should be taken into account when conducting the described experiments. Unless indicated otherwise, parts are parts by weight, temperature is degrees centigrade and pressure is at or near atmospheric. All components were obtained commercially unless otherwise indicated.

In each of the stability tests set forth in the examples, five tablets per pull were tested for L. acidophilus stability testing with L. acidophilus alone; five tablets per pull were tested for B. animalis subsp. lactis stability testing with B. animalis subsp. lactis alone, and five tablets per pull were tested when L. acidophilus and B. animalis subsp. lactis were tested as a combined assay; and six tablets per pull were tested for samples where L. acidophilus and B. animalis subsp. lactis were individually assayed from the combined product. For the stability testing, weekly, biweekly, or monthly pulls were carried out until a reduction in assay count below $1\times10^6$ was observed (exceptions to this procedure are noted in the examples).

Example 1

Manufacture of L. Acidophilus Tablets

A batch of twenty L. acidophilus probiotic tablets were manufactured using the ingredients set forth in Table 1.

TABLE 1

| Ingredients | mg/tab | % w/w |
|---|---|---|
| L. acidophilus 100 billion colonies/gram | 50.0 | 10.0 |
| PHARMABURST ® C1 (carrier) | 440.0 | 88.0 |
| Magnesium stearate (lubricant) | 10.0 0 | 2.00 0 |
| Total | 500.0 | 100.00 |

The L. acidophilus tablets were prepared by direct compression on a single punch machine using ⅜" standard concave tooling. Hardness of the tablets was 8-10 kp (kilopond=kilogram/N=force exerted by one kg of mass at Earth gravity). The compressed tablets were put into 60 cc high-density polyethylene ("HDPE") bottles and subjected to the controlled temperature of 25° C./60% RH. The product was subjected to microbiological stability testing at the following time intervals: 0 time, 1 month, 2 months, 4.5 months, 6 months, and 8.5 months. The results of the stability test are set forth in Table 2.

TABLE 2

| Time Periods Tested | L. acidophilus Stability (Presence of Anaerobe, Gram Positive Rod) Total Count/gm |
|---|---|
| 0 Time | $1.08 \times 10^{10}$ |
| 1 month | $6.3 \times 10^9$ |
| 2 months | $5.8 \times 10^9$ |
| 4.5 months | $3.2 \times 10^8$ |
| 6 months | $8.1 \times 10^5$ |
| 8.5 months | $5.2 \times 10^5$ |

Example 2

Manufacture of L. *Acidophilus* Tablets with Color, Flavor, and Sweetener

*L. acidophilus* probiotic tablets were prepared using the ingredients set forth in Table 3. Prior to tabletting, the *L. acidophilus* raw material was tested and found to have a microbial count of $1.8 \times 10^{11}$ colonies/gram.

TABLE 3

| Ingredients | Orange Flavored Tablets 800 Tablets | | Bubble Gum Flavored Tablets 600 Tablets | | Pineapple Flavored Tablets 700 Tablets | |
|---|---|---|---|---|---|---|
| | mg/tab | % w/w | mg/tab | % w/w | mg/tab | % w/w |
| *L. acidophilus* | 50.0 | 8.3333 | 50.0 | 8.3333 | 50.0 | 8.3333 |
| PHARMABURST ® C1 (carrier) | 539.3 | 89.8833 | 537.1 | 89.5167 | 535.9 | 89.3167 |
| Sucralose (ChemPoint.com, Seattle, WA) (sweetener) | 0.9 | 0.1500 | 0.9 | 0.1500 | 0.9 | 0.1500 |
| Spray dried natural and artificial flavor | 0.6 | 0.1000 | 1.8 | 0.3000 | 3.0 | 0.2000 |
| FD&C Colorant | 1.2 | 0.2000 | 1.2 | 0.2000 | 1.2 | 0.2000 |
| Magnesium Stearate (lubricant) | 8.0 | 1.3333 | 9.0 | 1.5000 | 9.0 | 1.5000 |
| Total | 600.0 | 100.0000 | 600.0 | 100.0000 | 600.0 | 100.0000 |

*Pink, Yellow, and Orange FD&C colorants were selected in amounts suitable to match a color to the selected flavor.

The orange and bubble gum flavored tablets were prepared by direct compression on a rotary machine using a ½" round standard concave tooling and the pineapple flavored tablets were prepared using a single punch press capsule-shaped tooling. The hardness of all of the tablets was in the range of 7-9 kp and disintegration times were all approximately 22 seconds.

The tablets of Table 3 were stored at 25° C./60% RH for stability testing without a desiccant, with a set of three tablets of each batch set aside as reserve samples for each flavor dosage form; the reserve samples were stored at 4° C. Table 4 sets forth the results of the monthly stability tests on the dosage forms of Table 3 over an 11-month period and Table 5 sets forth the results of the stability test of the reserve samples at month 13; five tablets were selected for each stability test pull. The stability of the *L. acidophilus* in the dosage forms was determined by measuring the presence of the gram-positive rod of *L. acidophilus*.

TABLE 4

| | L. acidophilus Stability (Presence of Anaerobic Gram-Positive Rod) Total Count/gram | | |
|---|---|---|---|
| Time Periods at 25° C./60% RH | Orange Flavored Tablets | Bubble Gum Flavored Tablets | Pineapple Flavored Tablets |
| 0 Time | $9.45 \times 10^9$ | $7.6 \times 10^9$ | $9.15 \times 10^9$ |
| 1 Month | $7.45 \times 10^9$ | $7.1 \times 10^9$ | $8.25 \times 10^9$ |
| 2 Month | $8.05 \times 10^9$ | $7.7 \times 10^9$ | $7.05 \times 10^9$ |
| 3 Month | $3.70 \times 10^9$ | $4.15 \times 10^9$ | $2.55 \times 10^9$ |
| 4 Month | $1.90 \times 10^9$ | $1.05 \times 10^9$ | $1.05 \times 10^9$ |
| 5 Month | $2.95 \times 10^8$ | $2.75 \times 10^8$ | $1.0 \times 10^8$ |
| 6 Month | $2.85 \times 10^8$ | $2.25 \times 10^8$ | $6.5 \times 10^7$ |
| 7 Month | $8.5 \times 10^7$ | $7.0 \times 10^7$ | $3.5 \times 10^7$ |
| 8 Month | $1.4 \times 10^7$ | $1.7 \times 10^7$ | $9.5 \times 10^6$ |
| 9 Month | $8.5 \times 10^5$ | $1.0 \times 10^6$ | $4.95 \times 10^5$ |
| 10 Month | $5.55 \times 10^5$ | $4.20 \times 10^5$ | $1.65 \times 10^5$ |
| 11 Months | $7.54 \times 10^4$ | $6.90 \times 10^4$ | $6.2 \times 10^4$ |

TABLE 5

| | L. acidophilus Stability (Presence of Anaerobe, Gram Positive Rod) Total Count/gram | | |
|---|---|---|---|
| Time Period at 4° C. | Orange Flavored Tablets | Bubble Gum Flavored Tablets | Pineapple Flavored Tablets |
| 13 Months | $7.53 \times 10^9$ | $4.65 \times 10^9$ | $7.55 \times 10^9$ |

As indicated in Table 4, at ten months, the total count of gram-positive rods of *L. acidophilus* in each flavor batch was less than $1 \times 10^6$; by contrast, the samples stored at 4° C. showed no reduction in microbial count at 13 months.

Example 3

Manufacture of *B. Animalis* Subsp. *Lactis* BB 12 Tablets

A batch of thirty *B. animalis* subsp. *lactis* strain BB 12 (hereinafter referred to as "*B. animalis* subsp. *lactis*") probiotic tablets were manufactured using the ingredients set forth in Table 6.

TABLE 6

| Ingredients | mg/tab | % w/w |
| --- | --- | --- |
| *B. animalis* subsp. *lactis* 100 billion colonies/gram | 50.0 | 10.0 |
| PHARMABURST ® C1 (carrier) | 442.50 | 88.50 |
| Magnesium stearate (lubricant) | 7.50 0 | 1.50 0 |
| Total | 500.0 | 100.00 |

The *B. animalis* subsp. *lactis* tablets were prepared by direct compression on a rotary machine using 7/16" standard concave tooling. Hardness of the tablets was in the range of 10-12 kp. The compressed tablets were put into 60 cc HDPE bottles without a desiccant and exposed to the controlled temperature of 25° C./60% RH. Five tablets per pull were subjected to microbiological stability testing at the following time intervals: 0 time, 1 month, 2 months, and 3 months. The results of the stability test are set forth in Table 7.

TABLE 7

| Time Period at 25° C./60% RH | *B. animalis* subsp. *lactis* Stability (Presence of Anaerobe, Gram Positive Rod) Total Count/gram |
| --- | --- |
| 0 Time | $3.8 \times 10^9$ |
| 1 month | $3.9 \times 10^6$ |
| 2 months | $2.1 \times 10^5$ |
| 3 months | $1.9 \times 10^5$ |

The results of the stability testing were below $1 \times 10^6$ at the two-month pull, but were continued for an additional month.

Example 4

Manufacture of *L. Acidophilus* Tablets with Color, Flavor, and Sweetener

Probiotic tablets (2000 tablets per flavor batch) containing both *L. acidophilus* and *B. animalis* subsp. *lactis* probiotic were prepared using the ingredients set forth in Table 8.

TABLE 8

| | Orange Flavored Tablets 2000 Tablets | | Bubblegum Flavored Tablets 2000 Tablets | | Pineapple Flavored Tablets 2000 Tablets | |
| --- | --- | --- | --- | --- | --- | --- |
| Ingredients | mg/tab | % w/w | mg/tab | % w/w | mg/tab | % w/w |
| *L. acidophilus* 100 billion colonies/gram | 50.00 | 7.69 | 50.00 | 7.69 | 50.00 | 7.69 |
| *B. animalis* subsp. *lactis* 100 billion colonies/gram | 50.00 | 7.69 | 50.00 | 7.69 | 50.00 | 7.69 |
| PHARMABURST ® C1 (carrier) | 537.3 | 82.66 | 536.10 | 82.48 | 534.90 | 82.29 |
| Sucralose (sweetener) | 0.90 | 0.14 | 0.90 | 0.14 | 0.90 | 0.14 |
| Spray dried natural & artificial flavor | 0.60 | 0.09 | 1.80 | 0.28 | 3.00 | 0.46 |
| FD & C Colorant | 1.20 | 0.18 | 1.20 | 0.18 | 1.20 | 0.18 |
| Magnesium Stearate (lubricant) | 10.0 | 1.54 | 10.00 | 1.54 | 10.00 | 1.54 |
| Total | 650.0 | 100.0 | 650.00 | 100.00 | 650.00 | 100.00 |

The tablets were prepared by direct compression on a rotary machine using a ½" round standard concave tooling. The hardness of the tablets was in the range of 8-10 kp. The compressed tablets were packaged into 180 cc HDPE bottles of 100 tablets each without a desiccant and exposed to the controlled temperature of 25° C./60% RH. The product was subjected to monthly microbiological stability testing over a period of 12 months or until a reduction in the assay count below $1 \times 10^6$ was observed. Six tablets per pull were analyzed at 0 time and 1 month for both *L. acidophilus* and *B. animalis* subsp. *lactis* and five tablets per pull were tested for *L. acidophilus* and *B. animalis* subsp. *lactis* independently for the remaining time periods. The results of the stability test are set forth in Tables 9 and 10, respectively.

TABLE 9

| | *L. acidophilus* and *B. animalis* subsp. *lactis* Stability (Presence of Anaerobe, Gram Positive Rod) Total Count/gram | | |
| --- | --- | --- | --- |
| Time Period at 25° C./60% RH | Orange Flavored Tablets | Bubble Gum Flavored Tablets | Pineapple Flavored Tablets |
| 0 Time | $4.2 \times 10^9$ | $3.35 \times 10^9$ | $4.45 \times 10^9$ |
| 1 Month | $4.3 \times 10^9$ | $3.8 \times 10^9$ | $4.2 \times 10^9$ |

TABLE 10

| Time Period at | Stability (Presence of Anaerobe, Gram Positive Rod) Total Count/gram | | | | | |
|---|---|---|---|---|---|---|
| | Orange Flavored Tablets | | Bubble Gum Flavored Tablets | | Pineapple Flavored Tablets | |
| 25° C./60% RH | Lacto | Bifido | Lacto | Bifido | Lacto | Bifido |
| 2 Months | $1.19 \times 10^9$ | $1.18 \times 10^9$ | $1.08 \times 10^9$ | $1.02 \times 10^9$ | $1.18 \times 10^9$ | $1.19 \times 10^9$ |
| 3 Months | $1.8 \times 10^9$ | $2.15 \times 10^9$ | $1.95 \times 10^9$ | $1.65 \times 10^9$ | $2.35 \times 10^9$ | $2.0 \times 10^9$ |
| 4 Months | $5.6 \times 10^8$ | $6.7 \times 10^8$ | $7.75 \times 10^8$ | $7.2 \times 10^8$ | $6.15 \times 10^8$ | $7.05 \times 10^8$ |
| 5 Months | $6.95 \times 10^7$ | $6.9 \times 10^7$ | $5.85 \times 10^7$ | $6.15 \times 10^7$ | $5.55 \times 10^7$ | $4.0 \times 10^7$ |
| 6 Months | $5.8 \times 10^6$ | $4.2 \times 10^6$ | $3.15 \times 10^6$ | $2.05 \times 10^6$ | $3.9 \times 10^6$ | $3.45 \times 10^6$ |
| 7 Months | $2.05 \times 10^6$ | $3.0 \times 10^6$ | $2.86 \times 10^6$ | $1.4 \times 10^6$ | $1.95 \times 10^5$ | $2.1 \times 10^5$ |
| 8 Months | $2.8 \times 10^5$ | $2.95 \times 10^5$ | $2.6 \times 10^5$ | $2.5 \times 10^5$ | $4.15 \times 10^4$ | $4.25 \times 10^4$ |

As noted in Table 10, after 8 months, the orange flavored tablets and the bubble gum flavored tablets yielded less than $1.0 \times 10^6$ total counts/gram of gram positive rods and after 7 months, the pineapple flavored tablets yielded less than $1 \times 10^6$ total counts/gram of gram positive rods; accordingly, the stability study was discontinued after the eight-month pull.

Example 5

Composite Packaging without Desiccant

The three flavor batches of Example 4 were tested for stability in a composite packaging of 100 tablets (33 of each flavor plus one additional tablet randomly selected) without a desiccant by placing the composite packaging in a 180 cc HDPE bottle at the controlled temperature of 25° C./60% RH and testing the tablets for microbiological stability each month for a period of 12 months or until an assay count below $1 \times 10^6$ was observed. Five tablets per pull (randomly selected from each flavor) were analyzed for total count of *L. acidophilus* and *B. animalis* subsp. *lactis* combined at 1 month and six tablets per pull (randomly selected from each flavor) were analyzed for *L. acidophilus* and *B. animalis* subsp. *lactis* independently for the remaining time periods (in this experiment, the typical six tablet per pull per for the combined pulled probiotic and five tablet per pull for the independently pulled probiotic was reversed). The results of the stability tests are set forth in Tables 11 and 12, respectively.

TABLE 11

| Time Period at 25° C./60% RH | Stability (Presence of Anaerobe, Gram Positive Rod) Total Count/gram |
|---|---|
| 1 Month | $4.55 \times 10^9$ |

TABLE 12

| Time Period at | Stability (Presence of Anaerobe, Gram Positive Rod) Total Count/gram | |
|---|---|---|
| 25° C./60% RH | *L. acidophilus* | *B. animalis* subsp. *lactis* |
| 2 Months | $4.55 \times 10^9$ | $5.50 \times 10^9$ |
| 3 Months | $1.5 \times 10^9$ | $1.75 \times 10^9$ |
| 4 Months | $3.2 \times 10^8$ | $3.3 \times 10^8$ |
| 5 Months | $5.35 \times 10^6$ | $9.1 \times 10^6$ |
| 6 Months | $3.5 \times 10^5$ | $1.9 \times 10^5$ |
| 7 Months | $1.3 \times 10^5$ | $1.75 \times 10^5$ |

The results of the stability testing were below $1 \times 10^6$ after six months, but were continued for an additional month.

Example 6

Composite Packaging with Desiccant

The three flavor batches of Example 6 were tested for stability in a composite packaging of 100 tablets (33 of each flavor plus one additional tablet randomly selected) with a desiccant by placing the composite packaging in a 180 cc HDPE bottle at the controlled temperature of 25° C./60% RH and testing the tablets for microbiological stability at 3 months, 6 months, 9 months, and 12 months, or until an assay count below $1 \times 10^6$ was observed. The tablets were analyzed for *L. acidophilus* and *B. animalis* subsp. *lactis* independently. The results of the stability test are set forth in Table 13.

TABLE 13

| Time Period at | Stability (Presence of Anaerobe, Gram Positive Rod) Total Count/gram | |
|---|---|---|
| 25° C./60% RH | *L. acidophilus* | *B. animalis* subsp. *lactis* |
| 3 Months | $1.34 \times 10^9$ | $1.32 \times 10^9$ |
| 6 Months | $2.65 \times 10^5$ | $2.05 \times 10^5$ |

The results of the stability testing were below $1 \times 10^6$ after six months; accordingly, the study was discontinued after the six-month pull.

Example 7

Manufacture of Probiotic Dosage Form with *L. Acidophilus*, *B. Animalis* Subsp. *Lactis*, Lactitol (Prebiotic), and OPC from Grape Seed Extract (Antioxidant)

Batches of orange flavored tablets were manufactured with PHARMABURST® C1, one of two lactitol prebiotics, i.e., CM 50 at 7.7% or FINLAC® DC (Xyrofin Oy Corp., Helsinki, Finland) at 39.7% with a corresponding decrease in PHARMABURST® C1, and OPC from grape seed extract. The batches were used to test the following parameters: (1) the organoleptic characteristics of lactitol and OPC containing products; (2) the effect of the prebiotic lactitol on probiotic stability; and (3) the effect of OPC on probiotic stability. The ingredients set forth in manufacturing the tablets for each batch are set forth in Table 14; the heading for each batch specifies the lactitol sweetener used and the number of tablets per batch.

TABLE 14

| Ingredients | Batch No. 1 7.7% Lactitol (CM 50) 800 Tablets | | Batch No. 2 39.7% Lactitol (FINLAC ® DC) 800 Tablets | | Batch No. 3 7.7% Lactitol (CM 50) 1500 Tablets | | Batch No. 4 39.7% Lactitol (FINLAC ® DC) 1500 Tablets | |
|---|---|---|---|---|---|---|---|---|
| | mg/tab | % w/w | mg/tab | % w/w | mg/tab | % w/w | mg/tab | % w/w |
| *L. acidophilus* | 50.00 | 7.69 | 50.00 | 7.69 | 50.00 | 7.69 | 50.00 | 7.69 |
| *B. animalis* subsp. *lactis* | 50.00 | 7.69 | 50.00 | 7.69 | 50.00 | 7.69 | 50.00 | 7.69 |
| OPC from grape seed extract (antioxidant) | 10.00 | 1.54 | 10.00 | 1.54 | — | — | — | — |
| PHARMABURST ® C1 (carrier) | 477.60 | 73.48 | 269.30 | 41.43 | 487.60 | 75.02 | 279.30 | 42.97 |
| Lactitol (prebiotic) | 50.00 | 7.69 | 258.30 | 39.74 | 50.00 | 7.69 | 258.30 | 39.74 |
| Sucralose (sweetener) | 0.60 | 0.09 | 0.60 | 0.09 | 0.60 | 0.09 | 0.60 | 0.09 |
| Spray dried natural & artificial orange flavor | 0.60 | 0.09 | 0.60 | 0.09 | 0.60 | 0.09 | 0.60 | 0.09 |
| FD & C yellow No. 6 Al lake | 1.20 | 0.18 | 1.20 | 0.18 | 1.20 | 0.18 | 1.20 | 0.18 |
| Magnesium Stearate (lubricant) | 10.00 | 1.54 | 10.00 | 1.54 | 10.00 | 1.54 | 10.00 | 1.54 |
| Total | 650.00 | 100.00 | 650.00 | 100.00 | 650.00 | 100.00 | 650.00 | 100.00 |

The tablets of Table 14 were made by direct compression on a rotary machine using a ½" round standard concave tooling. The hardness of the tables was in the range of 8-10 kp. One hundred of the compressed tablets from each batch were packaged into 180 cc HDPE bottles and stability tested at a controlled temperature until a reduction in the assay count was observed. Table 15 provides the parameters for the stability testing of Batches 1 to 4 from Table 14 and includes for each testing lot: the controlled temperature used, the time periods of testing, and whether or not a desiccant was used. All samples were also tested at 0 time in addition to the time periods specified in Table 15.

TABLE 15

| Batch No. | Testing Lot | Storage Condition | Time Periods for Sampling | Desiccant |
|---|---|---|---|---|
| Batch No. 1 | Test Lot 1 | 25° C./60% RH | 3, 6, 9, 10 months | Yes |
| Batch No. 1 | Test Lot 2 | 25° C./60% RH | 3, 6, 9, 10 months | No |
| Batch No. 1 | Test Lot 3 | 30° C./65% RH | monthly | Yes |
| Batch No. 1 | Test Lot 4 | 30° C./65% RH | monthly | No |
| Batch No. 2 | Test Lot 1 | 25° C./60% RH | 3, 6, 9, 10 months | Yes |
| Batch No. 2 | Test Lot 2 | 25° C./60% RH | 3, 6, 9, 10 months | No |
| Batch No. 2 | Test Lot 3 | 30° C./65% RH | monthly | Yes |
| Batch No. 2 | Test Lot 4 | 30° C./65% RH | monthly | No |
| Batch No. 3 | Test Lot 1 | 25° C./60% RH | 3, 6, 9, 10 months | Yes |
| Batch No. 3 | Test Lot 2 | 25° C./60% RH | 3, 6, 9, 10 months | No |
| Batch No. 3 | Test Lot 3 | 30° C./65% RH | monthly | Yes |
| Batch No. 3 | Test Lot 4 | 30° C./65% RH | monthly | No |
| Batch No. 3 | Test Lot 5 | 40° C./75% RH | 2, 4, and 6 weeks | Yes |
| Batch No. 3 | Test Lot 6 | 40° C./75% RH | 2, 4, and 6 weeks | No |
| Batch No. 4 | Test Lot 1 | 25° C./60% RH | 3, 6, 9, 10 months | Yes |
| Batch No. 4 | Test Lot 2 | 25° C./60% RH | 3, 6, 9, 10 months | No |
| Batch No. 4 | Test Lot 3 | 30° C./65% RH | monthly | Yes |
| Batch No. 4 | Test Lot 4 | 30° C./65% RH | monthly | No |
| Batch No. 4 | Test Lot 5 | 40° C./75% RH | 2, 4, and 6 weeks | Yes |
| Batch No. 4 | Test Lot 6 | 40° C./75% RH | 2, 4, and 6 weeks | No |

The results of the stability count for the testing lots of Table 15 are set forth in Table 16.

TABLE 16

BATCH NOS. 3 AND 4, TEST LOTS 5 AND 6
BI-WEEKLY PULLS AT 40° C./75% RH
WITH OR WITHOUT DESICCANT

| | Stability (Presence of Anaerobe, Gram Positive Rod) Total Count/gram | | | |
|---|---|---|---|---|
| | Batch 3 7.7% Lactitol/No OPC | | Batch 4 39.7% Lactitol/No OPC | |
| Time Periods at 40° C./75% RH | Lacto | Bifido | Lacto | Bifido |
| 0 Time | $3.95 \times 10^9$ | $4.30 \times 10^9$ | $3.30 \times 10^9$ | $2.80 \times 10^9$ |
| Test Lot 5 2 weeks (desiccant) | $4.65 \times 10^8$ | $6.75 \times 10^8$ | $4.9 \times 10^8$ | $6.4 \times 10^8$ |
| Test Lot 6 2 weeks (no desiccant) | $5.65 \times 10^8$ | $6.75 \times 10^8$ | $4.05 \times 10^8$ | $5.25 \times 10^8$ |
| 4 weeks Test Lot 5 (desiccant) | $1.87 \times 10^6$ | $1.81 \times 10^7$ | $2.3 \times 10^7$ | $2.8 \times 10^7$ |

TABLE 16-continued

BATCH NOS. 3 AND 4, TEST LOTS 5 AND 6 BI-WEEKLY PULLS AT 40° C./75% RH WITH OR WITHOUT DESICCANT

| | Stability (Presence of Anaerobe, Gram Positive Rod) Total Count/gram | | | |
|---|---|---|---|---|
| | Batch 3 7.7% Lactitol/No OPC | | Batch 4 39.7% Lactitol/No OPC | |
| Time Periods at 40° C./75% RH | Lacto | Bifido | Lacto | Bifido |
| Test Lot 6 4 weeks (no desiccant) | $2.18 \times 10^8$ | $3.20 \times 10^8$ | $7.4 \times 10^7$ | $9.35 \times 10^7$ |
| Test Lot 5 6 weeks (desiccant) | $3.75 \times 10^5$ | $5.6 \times 10^5$ | $1.0 \times 10^5$ | $1.9 \times 10^5$ |
| Test Lot 6 6 weeks (no desiccant) | $1.01 \times 10^7$ | $1.14 \times 10^7$ | $1.35 \times 10^5$ | $1.45 \times 10^5$ |

At six weeks, Test Lot 6 from Batch 3 (7.7% lactitol, no OPC, no desiccant) had stability readings above $1 \times 10^7$, indicating that the 7.7% lactitol (i.e., CM 50) and the absence of a desiccant has a positive effect on the probiotic stability of the dosage form when compared to comparable dosage forms prepared with 39.7% lactitol (i.e., FINLAC®) and/or are stored with a desiccant. At 6 weeks, the results for Test Lot 5 from Batch 3 and Test Lots 5 and 6 from Batch 4 were all below $1 \times 10^6$.

TABLE 17

BATCH NOS. 1, 2, 3 AND 4, TEST LOTS 3 AND 4 MONTHLY PULLS AT 30° C./65% RH WITH OR WITHOUT DESICCANT

| | Stability (Presence of Anaerobe, Gram Positive Rod) Total Count/gram | | | | | | | |
|---|---|---|---|---|---|---|---|---|
| | Batch No 1 7.7% Lactitol OPC | | Batch No. 2 39.7% Lactitol OPC | | Batch No. 3 7.7% Lactitol no OPC | | Batch No. 4 39.7% Lactitol no OPC | |
| Time Periods at 30° C./65% RH | Lacto | Bifido | Lacto | Bifido | Lacto | Bifido | Lacto | Bifido |
| 0 Time | $1.85 \times 10^9$ | $1.25 \times 10^9$ | $1.75 \times 10^9$ | $1.80 \times 10^9$ | $3.95 \times 10^9$ | $4.30 \times 10^9$ | $3.30 \times 10^9$ | $2.80 \times 10^9$ |
| 1 month Test Lot 3 (desiccant) | $6.2 \times 10^8$ | $6.1 \times 10^8$ | $6.85 \times 10^8$ | $5.2 \times 10^8$ | $1.16 \times 10^9$ | $1.15 \times 10^9$ | $1.06 \times 10^9$ | $1.08 \times 10^9$ |
| 1 month Test Lot 4 (no desiccant) | $7.6 \times 10^8$ | $6.15 \times 10^8$ | $6.9 \times 10^8$ | $7.75 \times 10^8$ | $8.45 \times 10^8$ | $6.75 \times 10^8$ | $1.01 \times 10^9$ | $9.5 \times 10^8$ |
| 2 months Test Lot 3 (desiccant) | $1.75 \times 10^7$ | $4.0 \times 10^7$ | — | — | $1.45 \times 10^7$ | $6.45 \times 10^7$ | $6.2 \times 10^7$ | $9.6 \times 10^7$ |
| 2 months Test Lot 4 (no desiccant) | — | — | $1.17 \times 10^8$ | $1.69 \times 10^8$ | — | — | — | — |
| 3 months Test Lot 3 (desiccant) | $7.95 \times 10^6$ | $1.9 \times 10^6$ | $5.85 \times 10^6$ | $4.1 \times 10^6$ | $7.7 \times 10^4$ | $1.2 \times 10^5$ | $4.75 \times 10^6$ | $9.05 \times 10^6$ |
| 3 months Test Lot 4 (no desiccant) | $6.0 \times 10^6$ | $5.0 \times 10^6$ | $6.85 \times 10^6$ | $4.55 \times 10^6$ | $1.50 \times 10^6$ | $1.26 \times 10^6$ | $1.25 \times 10^6$ | $1.9 \times 10^6$ |
| 4 months Test Lot 3 (desiccant) | $5.45 \times 10^5$ | $4.25 \times 10^5$ | $3.7 \times 10^5$ | $4.8 \times 10^5$ | $3.4 \times 10^5$ | $2.9 \times 10^5$ | $5.35 \times 10^5$ | $3.2 \times 10^5$ |
| 4 months Test Lot 4 (no desiccant) | $3.3 \times 10^6$ | $3.65 \times 10^6$ | $4.1 \times 10^6$ | $4.1 \times 10^6$ | $2.8 \times 10^6$ | $2.05 \times 10^6$ | $2.5 \times 10^6$ | $2.0 \times 10^6$ |
| 5 months Test Lot 3 (desiccant) | $4.35 \times 10^5$ | $1.95 \times 10^5$ | $2.9 \times 10^5$ | $2.95 \times 10^5$ | $4.2 \times 10^5$ | $2.5 \times 10^5$ | $1.7 \times 10^5$ | $2.45 \times 10^5$ |
| 5 months Test Lot 4 (no desiccant) | $4.8 \times 10^5$ | $5.95 \times 10^5$ | $2.25 \times 10^5$ | $2.35 \times 10^5$ | $2.5 \times 10^5$ | $2.5 \times 10^5$ | $2.1 \times 10^5$ | $3.1 \times 10^5$ |

TABLE 17-continued

BATCH NOS. 1, 2, 3 AND 4, TEST LOTS 3 AND 4
MONTHLY PULLS AT 30° C./65% RH WITH OR WITHOUT DESICCANT

Stability
(Presence of Anaerobe, Gram Positive Rod)
Total Count/gram

| Time Periods at 30° C./65% RH | Batch No 1 7.7% Lactitol OPC | | Batch No. 2 39.7% Lactitol OPC | | Batch No. 3 7.7% Lactitol no OPC | | Batch No. 4 39.7% Lactitol no OPC | |
|---|---|---|---|---|---|---|---|---|
| | Lacto | Bifido | Lacto | Bifido | Lacto | Bifido | Lacto | Bifido |
| 6 months Test Lot 3 (desiccant) | $8.35 \times 10^4$ | $8.35 \times 10^4$ | $1.60 \times 10^5$ | $1.76 \times 10^5$ | $1.29 \times 10^5$ | $1.26 \times 10^5$ | $1.43 \times 10^5$ | $1.67 \times 10^5$ |
| 6 months Test Lot 4 (no desiccant) | $1.55 \times 10^5$ | $1.54 \times 10^5$ | $1.04 \times 10^5$ | $1.01 \times 10^5$ | $1.26 \times 10^5$ | $1.14 \times 10^5$ | $1.37 \times 10^5$ | $1.29 \times 10^5$ |

After five months, the results of all test lots are below $1 \times 10^6$. The stability studies for Batch No. 1, Test Lots 3 and 4 (with and without a desiccant) were discontinued after the six-month pull and the stability studies for the remaining test lots were discontinued after the five-month pull.

The results of Table 17 show that Test Lot 4 from Batch 1 (7.7% lactitol, OPC, no desiccant) had slightly increased probiotic stability over the remaining test lots.

The results of Table 18 show that up to 3 months, all Test Lots tested relatively consistently, with Batch 1, Test Lots 1 and 2 (7.7% lactitol, OPC, with and without desiccant), having the highest counts. At 6 months, Batch No. 1, Test Lot 1 (7.7% lactitol, OPC, with desiccant) had the highest number of viable colonies of both *L. acidophilus* and *B. animalis* subsp. *lactis*. At nine months, however, Batch No. 1, Test Lot 1, did not have any positive colonies, while Test

TABLE 18

BATCH NOS. 1, 2, 3 AND 4, TEST LOTS 1 AND 2
MONTHLY PULLS AT 25° C./60% RH WITH OR WITHOUT DESICCANT

Stability
(Presence of Anaerobe, Gram Positive Rod)
Total Count/gram

| Time Periods at 25° C./60% RH | Batch No 1 7.7% Lactitol OPC | | Batch No. 2 39.7% Lactitol OPC | | Batch No. 3 7.7% Lactitol no OPC | | Batch No. 4 39.7% Lactitol no OPC | |
|---|---|---|---|---|---|---|---|---|
| | Lacto | Bifido | Lacto | Bifido | Lacto | Bifido | Lacto | Bifido |
| 0 Time | $1.85 \times 10^9$ | $1.25 \times 10^9$ | $1.75 \times 10^9$ | $1.80 \times 10^9$ | $3.95 \times 10^9$ | $4.30 \times 10^9$ | $3.30 \times 10^9$ | $2.80 \times 10^9$ |
| 3 months Test Lot 1 (desiccant) | $2.32 \times 10^7$ | $2.62 \times 10^7$ | $2.24 \times 10^7$ | $1.68 \times 10^7$ | $1.86 \times 10^7$ | $1.60 \times 10^7$ | $1.86 \times 10^7$ | $1.71 \times 10^7$ |
| 3 months Test Lot 2 (no desiccant) | $2.65 \times 10^7$ | $2.22 \times 10^7$ | $2.43 \times 10^7$ | $1.92 \times 10^7$ | $1.16 \times 10^7$ | $2.00 \times 10^7$ | $1.06 \times 10^7$ | $1.24 \times 10^7$ |
| 6 months Test Lot 1 (desiccant) | $8.35 \times 10^5$ | $8.35 \times 10^5$ | $1.60 \times 10^5$ | $1.76 \times 10^5$ | $1.29 \times 10^5$ | $1.26 \times 10^5$ | $1.43 \times 10^5$ | $1.67 \times 10^5$ |
| 6 months Test Lot 2 (no desiccant) | $1.55 \times 10^5$ | $1.54 \times 10^5$ | $1.04 \times 10^5$ | $1.01 \times 10^5$ | $1.26 \times 10^5$ | $1.14 \times 10^5$ | $1.37 \times 10^5$ | $1.29 \times 10^5$ |
| 9 months Test Lot 1 (desiccant) | 0 | 0 | $2.3 \times 10^3$ | 0 | $6.1 \times 10^6$ | $6.6 \times 10^6$ | $1.9 \times 10^6$ | $7.7 \times 10^5$ |
| 9 months Test Lot 2 (no desiccant) | 0 | 0 | $2.0 \times 10^1$ | 0 | 0 | 0 | 0 | 0 |
| 10 months Test Lot 1 (desiccant) | 0 | 0 | $3.15 \times 10^2$ | 0 | $3.3 \times 10^6$ | $3.9 \times 10^6$ | $1.06 \times 10^6$ | $4.3 \times 10^5$ |
| 10 months Test Lot 2 (no desiccant) | 0 | 0 | 0 | 0 | | | | |

Lots 3 (no OPC, desiccant) of both Batch Nos. 3 and 4 still had viable colonies of both bacterial species at ten months. At nine and ten months, Test Lot 3 of Batch 3 (7.7% lactitol, no OPC, desiccant) had a significantly higher count of viable species than did Test Lot 3 of Batch 4 (39.7% lactitol, no OPC, desiccant).

Example 8

Manufacture of Probiotic Dosage Form with *L. Acidophilus*, *B. Animalis* Subsp. *Lactis*, Vitamin A Palmitate, and Encapsulated Zinc Oxide A batch of 500 tablets of a mango-flavored combination probiotic dosage form containing *L. acidophilus*, *B. animalis* subsp. *lactis*, vitamin A, and zinc oxide was prepared with the ingredients set forth in Table 19.

TABLE 19

| Ingredients | Mango Flavored Tablets 500 Tablets | |
|---|---|---|
| | mg/tab | % w/w |
| *L. acidophilus* 100 billion colonies/gram | 50.00 | 7.46 |
| *B. animalis* subsp. *lactis* 100 billion colonies/gram | 50.00 | 7.46 |
| Encapsulated Zinc Oxide | 10.00 | 1.49 |
| Vitamin A Palmitate | 6.80 | 1.01 |
| PHARMABURST ® C1 (carrier) | 539.10 | 80.46 |
| Sucralose (sweetener) | 0.90 | 0.13 |
| P11040 Artificial Mango Flavor S.D. Powder | 2.00 | 0.30 |
| FD & C Colorant | 1.20 | 0.18 |
| Magnesium Stearate (lubricant) | 10.0 0 | 1.49 0 |
| Total | 670.0 | 100.00 |

The tablets were prepared by direct compression on a rotary machine using a ½" round standard concave tooling. The hardness of the tablets was in the range of 8-12 kp. The mango flavored tablets were stored with a desiccant and subjected to stability testing for *L. acidophilus* and *B. animalis* subsp. *lactis* independently at varying time points under three different storage conditions: 40° C./75% RH (Table 20); 35° C./65% RH (Table 21); and 25° C./60% RH (Table 22).

TABLE 20

| Time Period at | Stability (Presence of Anaerobe, Gram Positive Rod) Total Count/gram | |
|---|---|---|
| 40° C./75% RH | *L. acidophilus* | *B. animalis* subsp. *lactis* |
| 0 time | $4.6 \times 10^9$ | $5.45 \times 10^9$ |
| 2 weeks | $6.55 \times 10^8$ | $7.5 \times 10^8$ |
| 1 month | $2.25 \times 10^6$ | $3.65 \times 10^6$ |

TABLE 21

| Time Period at | Stability (Presence of Anaerobe, Gram Positive Rod) Total Count/gram | |
|---|---|---|
| 30° C./65% RH | *L. acidophilus* | *B. animalis* subsp. *lactis* |
| 0 time | $4.6 \times 10^9$ | $5.45 \times 10^9$ |
| 1 month | $3.6 \times 10^9$ | $3.4 \times 10^9$ |
| 2 months | $2.45 \times 10^8$ | $3.00 \times 10^8$ |
| 3 months | $2.26 \times 10^8$ | $2.05 \times 10^8$ |
| 8 months | $3.8 \times 10^5$ | $2.6 \times 10^6$ |
| 9 months | $3.1 \times 10^5$ | $1.58 \times 10^6$ |

TABLE 22

| Time Periods at | Stability (Presence of Anaerobe, Gram Positive Rod) Total Count/gram | |
|---|---|---|
| 25° C./60% RH | *L. acidophilus* | *B. animalis* subsp. *lactis* |
| 0 time | $4.6 \times 10^9$ | $5.45 \times 10^9$ |
| 3 months | $2.17 \times 10^8$ | $2.34 \times 10^8$ |
| 6 months | $1.91 \times 10^7$ | $1.87 \times 10^7$ |

Tables 21 and 22 show that the samples tested at 30° C./65% RH and 25° C./60% RH had very high stability counts at 3 months time and the samples tested at 25° C./60% RH had high stability counts at 6 months time indicating that the presence of vitamin A and zinc oxide may have a positive effect on the stability of the probiotic dosage form under these conditions during a 3 to 6 month time period. Comparatively, the values of the 3-month counts for the samples of Tables 21 and 22 are significantly higher than the values of the 3-month counts for the samples of Tables 17 and 18.

Example 9

Manufacture of Probiotic Dosage Form with *L. Acidophilus*, *B. Animalis* Subsp. *Lactis*, and OPC from Pine Bark Source A batch of 600 tablets of an orange-flavored combination probiotic dosage form containing *L. acidophilus*, *B. animalis* subsp. *lactis*, and OPC from pine bark was prepared with the ingredients set forth in Table 23.

TABLE 23

| Ingredients | Orange-Flavored Tablets 600 Tablets | |
|---|---|---|
| | mg/tab | % w/w |
| *L. acidophilus* 100 billion colonies/gram | 50.00 | 7.69 |
| *B. animalis* subsp. *lactis* 100 billion colonies/gram | 50.00 | 7.69 |
| OPC from Pine Bark (antioxidant) | 10.00 | 1.54 |
| Lactitol (FINLAC ® DC) (prebiotic) | 50.00 | 7.69 |
| PHARMABURST ® C1 (carrier) | 477.60 | 73.48 |
| Sucralose (sweetener) | 0.60 | 0.09 |
| Spray dried natural & artificial orange flavor | 0.60 | 0.09 |
| FD & C Yellow No. 6 Aluminum Lake | 1.20 | 0.18 |

TABLE 23-continued

| | Orange-Flavored Tablets 600 Tablets | |
|---|---|---|
| Ingredients | mg/tab | % w/w |
| Magnesium Stearate (lubricant) | 10.0 0 | 1.54 0 |
| Total | 650.0 | 100.00 |

The tablets were prepared by direct compression on a rotary machine using a ½" round standard concave tooling. The hardness of the tablets was in the range of 8-12 kp. The tablets as prepared were stored with a desiccant and subjected to stability testing for *L. acidophilus* and *B. animalis* subsp. *lactis* as set forth in Tables 24, 25, and 26.

TABLE 24

| Time Periods at 40° C./75% RH | Stability (Presence of Anaerobe, Gram Positive Rod) Total Count/gram | |
|---|---|---|
| | *L. acidophilus* | *B. animalis* subsp. *lactis* |
| 0 time | $1.06 \times 10^9$ | $1.08 \times 10^9$ |
| 2 weeks | $1.06 \times 10^8$ | $7.2 \times 10^7$ |
| 1 month | $1.9 \times 10^6$ | $1.1 \times 10^6$ |
| 2 months | $2.2 \times 10^5$ | $2.35 \times 10^5$ |

TABLE 25

| Time Periods at 30° C./65% RH | Stability (Presence of Anaerobe, Gram Positive Rod) Total Count/gram | |
|---|---|---|
| | *L. acidophilus* | *B. animalis* subsp. *lactis* |
| 0 time | $1.06 \times 10^9$ | $1.08 \times 10^9$ |
| 1 month | $4.3 \times 10^8$ | $4.65 \times 10^8$ |
| 2 months | $5.25 \times 10^8$ | $5.8 \times 10^8$ |
| 3 months | $2.4 \times 10^8$ | $2.35 \times 10^8$ |
| 4 months | $4.0 \times 10^6$ | $2.8 \times 10^6$ |
| 6 months | 0 | 0 |

TABLE 26

| Time Periods at 25° C./60% RH | Stability (Presence of Anaerobe, Gram Positive Rod) Total Count/gram | |
|---|---|---|
| | *L. acidophilus* | *B. animalis* subsp. *lactis* |
| 0 time | $1.06 \times 10^9$ | $1.08 \times 10^9$ |
| 3 months | $8.0 \times 10^8$ | $7.75 \times 10^8$ |
| 6 months | $1.7 \times 10^8$ | $1.5 \times 10^8$ |
| 9 months | $9.4 \times 10^7$ | $3.1 \times 10^7$ |

Table 25 shows a high percentage of live colonies of both bacterial species at 30° C./65% RH at 6 months and Table 26 shows a very high percentage of live colonies of both bacterial species at 25° C./60% RH at 9 months, indicating that perhaps the OPC from pine bark enhances the stability of the probiotic dosage forms under the specified conditions.

Comparatively, the values of the 3-month counts for the samples of Tables 25 and 26 (OPC from pine bark, FINLAC® lactitol, desiccant) are significantly higher than the values of the 3-month counts for the samples of Batch 2, Test Lot 2 (OPC from grape seed, FINLAC® lactitol, desiccant) in Tables 17 and 18.

Example 10

Stability Assessment of *L. Acidophilus* Together with Mannitol and/or Sorbitol

Two batches of 200 probiotic tablets were prepared with *L. acidophilus* and mannitol (Batch A) and *L. acidophilus* and sorbitol (Batch B) Table 27 sets forth the ingredients that were used to prepare the tablets.

TABLE 27

| | Batch A Mannitol 200 Tablets | | Batch B Sorbitol 200 Tablets | |
|---|---|---|---|---|
| Ingredients | mg/tab | % w/w | mg/tab | % w/w |
| *L. acidophilus* | 50.0 | 10.00 | 50.00 | 10.00 |
| Mannitol | 440.0 | 88.00 | — | — |
| Sorbitol | — | — | 440.0 | 88.00 |
| Magnesium Stearate (lubricant) | 10.0 0 | 2.00 0 | 10.00 0 | 2.00 0 |
| Total | 500.00 | 100.00 | 500.00 | 100.00 |
| Tablet Hardness | 5-7 kp | | 24-27 kp | |

Tablets were made by direct compression on a rotary machine using a ½" round standard concave tooling. As shown in Tablet 27, the hardness of the tablets varied dramatically due to the characteristics of mannitol and sorbitol. Table 28 shows the results of the stability assay for *L. acidophilus* at 40° C./75% RH without a desiccant at three time points.

TABLE 28

| | *L. acidophilus* Stability (Presence of Anaerobe, Gram Positive Rod) Total Count/gm | |
|---|---|---|
| Time Periods at 40° C./75% RH | Batch A Mannitol | Batch B Sorbitol |
| 0 time | $2.65 \times 10^8$ | $4.1 \times 10^8$ |
| 3 weeks | 0 | 0 |
| 1 month | 0 | 0 |

The results of Table 28 show that the probiotic cultures in the tablets failed to survive storage at 40° C./75% RH indicating that-mannitol and sorbitol alone have no effect on the stability of *L. acidophilus* at 40° C./75% RH.

As a control for the testing of Batches A and B, probiotic formulations were prepared with the carriers PHARMABURST® C1 (Batch C; SPI Polyols, New Castle, Del.) and STARCH 1500® (Batch D; Colorcon, Inc., West Point, Pa.). The ingredients for the control formulations are set forth in Table 29.

TABLE 29

|  | Batch C STARCH 1500® 200 Tablets | | Batch D PHARMABURST® 200 Tablets | |
|---|---|---|---|---|
| Ingredients | mg/tab | % w/w | mg/tab | % w/w |
| L. acidophilus | 50.0 | 10.00 | 50.00 | 10.00 |
| PHARMABURST® C1 (carrier) | — | — | 440.0 | 88.00 |
| STARCH 1500® (carrier) | 440.0 | 88.00 |  |  |
| Magnesium Stearate (lubricant) | 10.0 0 | 2.00 0 | 10.00 0 | 2.00 0 |
| Total | 500.00 | 100.00 | 500.00 | 100.00 |
| Tablet Hardness | 2-3 Kp | | 8-10 Kp | |

Tablets were made by direct compression on a rotary machine using a ½" round standard concave tooling. The hardness of the tablets varied with the characteristics of each formulation. The control batches were stored for two weeks at 40° C./75% RH without a desiccant and tested for *L. acidophilus* at two time periods, which are set forth in Table 30.

TABLE 30

| | *L. acidophilus* Stability (Presence of Anaerobe, Gram Positive Rod) Total Count/gram | |
|---|---|---|
| Time Periods at 25° C./60% RH | Batch C STARCH 1500® | Batch D PHARMABURST® |
| 0 time | $4.45 \times 10^8$ | $3.0 \times 10^9$ |
| 2 weeks | $8.2 \times 10^3$ | $2.65 \times 10^3$ |
| 1 month | 0 | 0 |

The results of Table 30 show that the presence of PHARMABURST® alone provides a limited increase in the increase of the probiotic dosage from 0 time to 2 weeks at 25° C./60% RH.

Example 11

Testing for Pharmaburst®, Lactitol, and OPC Synergism on Probiotic Stability

To determine if lactitol and OPCs have a synergistic effect with the PHARMABURST® carrier of Tables 29 and 30, thus enhancing stability of the *L. acidophilus* probiotic, four batches of tablets were prepared and tested under the harsh storage conditions of 40° C./75% RH. The following parallel formulations were manufactured: (1) PHARMABURST® C1 (abbreviated as "PHRMBRST" in Tables 31 and 32) and lactitol with magnesium stearate (Batch E); (2) PHARMABURST® C1 and lactitol with calcium stearate (Batch F); (3) PHARMABURST® C1 and pine bark OPC with lactitol (Batch G); and (4) PHARMABURST® C1 and pine bark OPC without lactitol (Batch H). All parallel formulations were placed on accelerated stability testing according to the formulations set forth in Table 31.

TABLE 31

|  | Batch E PHRMBRST®, Lactitol, and Mg Stearate 200 Tablets | | Batch F PHRMBRST®, Lactitol, and Ca Stearate 200 Tablets | | Batch G PHRMBRST®, Lactitol, OPC, and Mg Stearate 200 Tablets | | Batch H PHRMBRST® OPC, and Mg Stearate 200 Tablets | |
|---|---|---|---|---|---|---|---|---|
| Ingredients | mg/tab | % w/w | mg/tab | % w/w | mg/tab | % w/w | mg/tab | % w/w |
| L. acidophilus | 50.00 | 10.00 | 50.00 | 10.00 | 50.00 | 10.00 | 50.00 | 10.00 |
| PHARMABURST® C1 (carrier) | 390.00 | 78.00 | 390.00 | 78.00 | 384.00 | 76.40 | 434.00 | 86.80 |
| Lactitol (prebiotic) | 50.00 | 10.00 | 50.00 | 10.00 | 50.00 | 10.00 | — | — |
| OPC from Pine Bark (antioxidant) | — | — | — | — | 6.00 | 1.20 | 6.00 | 1.20 |
| Calcium Stearate | — | — | 10.00 | 2.00 | — | — | — | — |
| Magnesium Stearate | 10.00 | 2.00 | — | — | 10.00 | 2.00 | 10.00 | 2.00 |
| Total | 500.00 | 100.00 | 500.00 | 100.00 | 500.00 | 100.00 | 500.00 | 100.00 |
| Hardness | 8-10 kp | | 8-10 kp | | 8-10 kp | | 8-10 kp | |

Tablets were made by direct compression on a rotary machine using a ½" round standard concave tooling. The hardness of the tablets varied with the characteristics of each formulation. All samples were stored for one month at 40° C./75% RH without a desiccant and tested for *L. acidophilus* at the time periods specified in Table 32.

TABLE 32

*L. acidophilus* Stability
(Presence of Anaerobe, Gram Positive Rod)
Total Count/gram

| Time Periods at 40° C./75% RH | Batch E PHRMBRST®, Lactitol, and Mg Stearate | Batch F PHRMBRST®, Lactitol, and Ca Stearate | Batch G PHRMBRST®, Lactitol, OPC, and Mg Stearate | Batch H PHRMBRST®, OPC, and Ca Stearate |
|---|---|---|---|---|
| 0 time | $5.6 \times 10^9$ | $4.5 \times 10^9$ | $2.2 \times 10^9$ | $3.7 \times 10^9$ |
| 2 weeks | $1.59 \times 10^8$ | $3.55 \times 10^7$ | $1.61 \times 10^7$ | $4.95 \times 10^7$ |
| 1 month | 0 | 0 | 0 | 0 |

Example 12

The Effect of Lactitol and Pharmaburst® on *L. Acidophilus* Stability at 40° C./75% RH To test if a synergistic reaction is occurring between the lactitol and PHARMABURST® to result in increased stability of *L. acidophilus*, three additional batches of tablets (Batches I, J, and K) were formulated as set forth in Table 33; the stability results for the tablets in the three batches at 40° C./75% RH are set forth in Table 34.

TABLE 33

| Ingredients | Batch I Lactitol 200 Tablets mg/tab | % w/w | Batch J PHARMABURST® 200 Tablets mg/tab | % w/w | Batch K Lactitol and PHARMABURST®, 200 Tablets mg/tab | % w/w |
|---|---|---|---|---|---|---|
| *L. acidophilus* | 50.00 | 10.00 | 50.00 | 10.00 | 50.00 | 10.00 |
| PHARMABURST® C1 (carrier) | — | — | 440.00 | 88.00 | 40.00 | 8.00 |
| Lactitol (prebiotic) | 440.00 | 88.00 | — | — | 400.00 | 80.00 |
| Magnesium Stearate | 10.00 | 2.00 | 10.00 | 2.00 | 10.00 | 2.00 |
| Total | 500.00 | 100.00 | 500.00 | 100.00 | 500.00 | 100.00 |

TABLE 34

*L. acidophilus* Stability
(Presence of Anaerobe, Gram Positive Rod)
Total Count/gram

| Time Periods at 40° C./75% RH | Batch I Lactitol | Batch J PHARMABURST® | Batch K Lactitol and PHARMABURST® |
|---|---|---|---|
| 0 time | $4.5 \times 10^8$ | $4.4 \times 10^8$ | $4.1 \times 10^8$ |
| 2 weeks | 0 | $1.62 \times 10^3$ | $2.3 \times 10^2$ |

The results of Table 34 show that lactitol alone shows no viable *L. acidophilus* colonies after two weeks at 40° C./75% RH whereas PHARMABURST® alone and lactitol with even a relatively low weight percent of PHARMABURST® did show viable colonies at 2 weeks time under the harsh storage conditions of 40° C./75% RH.

We claim:

1. A method of enhancing stability of a uniformly blended probiotic composition comprising combining at least one probiotic species, mannitol, sorbitol, at least one prebiotic wherein the prebiotic is a sugar alcohol selected from the group consisting of erythritol, lactitol, maltitol, and xylitol, at least one disintegrant, and at least one glidant;

wherein the amount of mannitol in the composition is greater than the amount of the sorbitol, greater than the amount of the at least one disintegrant and greater than the amount of the at least one glidant, wherein the amount of sorbitol in the composition is greater than the amount of the at least one disintegrant and greater than the amount of the at least one glidant, wherein the amount of the at least one disintegrant in the composition is greater than the amount of the at least one glidant.

2. The method of claim 1, wherein the disintegrant is selected from the group consisting of sodium croscarmellose, crospovidone, gellan gum, hydroxypropyl cellulose, starch, and sodium starch glycolate.

3. The method of claim 1, wherein the glidant is selected from the group consisting of silicon dioxide, colloidal silicon dioxide, and talc.

4. The method of claim 1, further comprising combining a lubricant in the composition.

5. The method of claim 4, wherein the lubricant is selected from the group consisting of calcium stearate, magnesium stearate, stearic acid, sodium stearyl fumerate, and vegetable based fatty acids.

6. The method of claim 1, wherein the mannitol or sorbitol is present in the composition in a range of approximately 30% w/w to approximately 98% w/w.

7. The method of claim 1, wherein the at least one probiotic species is selected from the group consisting of *Lactobacillus acidophilus, L. bulgaricus, L. casei, L. paracasei, L. fermentum, L. plantarum, L. rhamnosus, L. salivarius, Bifidobacterium bifidum, B. infantis, B. animalis* subsp. *lactis, B. longum, Streptococcus thermophilis, Enterococcus faecalis,* and *E. faecium.*

8. The method of claim 7, wherein the at least one probiotic species is selected from *L. acidophilus, L. salivarius, B. animalis* subsp. *lactis,* and *S. thermophilis.*

9. The method of claim 1, wherein the composition comprises at least two probiotic species selected from *Lactobacillus acidophilus, Bifidobacterium animalis* subsp. *lactis,* and *Streptococcus thermophilis.*

10. The method of claim 1, wherein the at least one probiotic species is present in the composition in a range of approximately $10^6$ to approximately $10^{10}$ colonies per dosage unit.

11. The method of claim 1, further comprising combining a phytonutrient in the composition.

12. The method of claim 11, wherein the phytonutrient is an oligomeric proanthocyanidin (OPC).

13. The method of claim 12, wherein the OPC is extracted from grape seed or pine bark.

14. The method of claim 12, wherein the OPC is present in the composition in a range of approximately 0.5% w/w to approximately 10% w/w.

15. The method of claim 1, further comprising combining a vitamin in the composition, wherein the vitamin is selected from the group consisting of vitamin A (retinol), vitamin B1 (thiamine), vitamin B2 (riboflavin), vitamin B3 (niacin), vitamin B5 (pantothenic acid), vitamin B6 (pyridoxine), vitamin B, (biotin), vitamin B, (folic acid), vitamin B12 (cyanocobalamin), vitamin C (ascorbic acid), vitamin D1 (lamisterol), vitamin D2 (ergocalciferol), vitamin D3 (dihyrotachysterol), vitamin D4 (7-dehydrositosterol), vitamin E (tocopherol), and vitamin K (naphthoquinone).

16. The method of claim 1, further comprising combining a dietary mineral in the composition, wherein the dietary mineral is selected from the group consisting of calcium, chloride, magnesium, phosphorous, potassium, sodium, and sulfur.

17. The method of claim 1, further comprising combining a trace mineral in the composition, wherein the trace mineral is selected from the group consisting of chromium, cobalt, copper, fluorine, iodine, iron, manganese, molybdenum, selenium, and zinc.

* * * * *